United States Patent [19]

Williams

[11] Plant 4,925

[45] Nov. 9, 1982

[54] MINIATURE ROSE PLANT

[76] Inventor: Ernest D. Williams, 1510 Lebanon Ave., Dallas, Tex. 75208

[21] Appl. No.: 260,327

[22] Filed: May 4, 1981

[51] Int. Cl.[3] ..... A01H 5/00

[52] U.S. Cl. ..... Plt./9

[58] Field of Search ..... Plt./9

*Primary Examiner*—Robert E. Bagwill

[57] ABSTRACT

The subject of this disclosure is a new and distinct variety of miniature rose primarily distinguished by the light rose pink buds and flowers and by the bushy easy to propagate plant.

1 Drawing Figure

The present invention relates to a new and distinct variety of hardy, dwarf, bush type rose plant of the miniature class; the variety being primarily characterized—as to novelty—by light to medium rose pink buds and flowers which in general color effect are similar to but darker than Peaches 'N Cream (miniature—U.S. Plant Pat. No. 4,278).

The variety is further characterized by:

An abundance of bloom, with flowers usually borne singly (sometimes several to the stem).

Little or no fragrance.

A plant which is vigorous, of rounded much branched shape with small glossy foliage with pointed leaflets; the buds and flowers being similar in form and size to Peaches 'N Cream (miniature—U.S. Plant Pat. No. 4,278).

The plant, which has a normal height of 12–14 inches or more, can easily be maintained at lesser height by occasional trimming.

A plant which grows and blooms satisfactorily both in greenhouse and outdoors; is good for growing in pots; and provides excellent garden decoration as well as cut flowers.

The present variety of miniature rose was originated by me at my nursery located at Dallas, Tex., under conditions of careful control and observation, as a rose between Little Darling (U.S. Plant Pat. No. 1,581, expired—Floribunda) as the seed parent and Little Chief (miniature—not patented) as the pollen parent.

Subsequent to origination of the variety I successfully asexually reproduced it at my nursery, located as aforesaid, by cuttings, the reproductions having run true in all respects.

The color photograph illustrates the variety, including the foliage, buds and flowers.

Referring now specifically to the new and distinct variety of miniature rose plant, the following is a detailed description thereof in outline; all major color plate identifications being by reference to the British Colour Council Horticultural Colour Chart, except where common terms of color definition are employed.

Type: Hardy; dwarf; bushy; rounded; seedling; greenhouse; outdoors; cut flowers; garden decoration; potted plant.

Class: Miniature.

*Variety name.*—Amy's Delight.

Flowers borne: Singly (sometimes several together) on slender wirey stems.

Quantity of bloom: Abundant both outside and in greenhouse.

Bud:

*Peduncle.*—Medium length; slender but sturdy; erect; medium green, sometimes tinted bronze (outdoors); hairs — usually several.

*Before calyx breaks.*—Size — small.

*Form.*—Pointed ovoid with several small foliaceous parts extending beyond the tip of the bud equal to one-half or less of its length.

*Color.*—Medium green, occasionally tinted with bronze (outdoors).

*As calyx breaks.*—Color — rose pink — near Nyron Rose 623/1 or 623/2 (sometimes lighter pink to whitish at base). Opening: opens well in all weather.

Bloom:

*Size when fully open.*—Small, averaging about $1\frac{1}{4}$ inches.

*Petalage.*—Double — averaging about 50–60 petals, arranged regularly plus sometimes a few small petaloids.

*Form.*—Imbricated, becoming more rounded, with petals rolled loosely outward, and later at maturity full with petals rolled loosely outward and downward. Open flowers usually show no stamens.

Petals: Fairly thick; satiny on inside and on outside surface.

*Shape.*—Outside petals, broad lanceolate with rounded tip; intermediate — broad lanceolate with rounded tip; inside — lanceolate with short acute (nearly rounded) tip.

Color: Newly opened flower from a plant grown outdoors (September 1980), Dallas, Tex.:

*Outside petal.*—Outside surface — light rose pink, near Empire Rose 621/3 on upper $\frac{2}{3}$ of petal shading lighter at base. Inside surface — near Empire Rose 621/2 blending into near white on basal $\frac{1}{3}$ or less of petal (sometimes deeper shade in cooler weather).

*Intermediate petal.*—Outside surface — similar to outside petal. Inside surface — similar to outside petal.

*Inner petal.*—Outside surface same as intermediate petal; inside surface — same as intermediate petal.

*General color effect.*—Newly opened flowers — clear medium rose pink. Three days open — color similar to newly opened flowers. Behavior — opens well in all weather. Spent petals may or may not drop off. Flower longevity (September 1980) — plant in pot 4–6 days or longer. Cut flowers at living room temperature 3–5 days or longer.

*Reproductive organs:*

*Stamens.*—Few to none, arranged regularly about pistils.

*Filaments.*—Varying length, yellow.

*Anthers.*—Yellow.

*Pollen.*—Little or none.

*Pistils.*—Average number.

Styles.—Fairly even; medium length; bunched.

*Ovaries.*—All enclosed in calyx.

*Hips.*—None.

*Sepals.*—Permanent; spear shaped; recurved.

*Seed.*—None.

Foliage:

*Leaves.*—Compound of five (sometimes three or seven) leaflets; quite small; leathery; glossy.

*Leaflets.*—Shape: broad lanceolate — nearly oval; apex acute; base rounded or rounded acute. Margin serrate. Color: medium green; new growth — normal (medium) green. Rachis: medium strength; upper side may have several tiny short hairs, grooved; underside; may have several small thorns and some tiny hairs. Stipules: medium long; narrow to medium width; medium length; narrow points which turn out at more or less than 45 degrees.

Growth:

*Habit.*—Dwarf; bushy; rounded; much branched.

*Growth.*—Free vigorous; internodes short.

*Canes.*—Medium; slender; sturdy.

*Main stems.*—Color: medium green.

*Thorns.*—Average; slender; medium length; straight; color — tan. Prickles — none. Hairs — none.

*Branches.*—Color: light to medium green. Thorns: average; medium length; slender; straight, color — greenish. Medium to short oval base. Prickles — none. Hairs — none.

The miniature rose plant and its flowers as herein described may vary in slight detail due to climatic, soil and cultural conditions under which the variety may be grown; the present description being of the variety as grown at Dallas, Tex.

The following is claimed:

1. A new and distinct variety of miniature rose plant of hardy, dwarf, bushy, much branched habit, substantially as illustrated and described, characterized by buds and flowers which are medium to light rose pink in color, the buds and flowers resembling Peaches 'N Cream (miniature — U.S. Plant Pat. No. 4,278) in size and shape, but more double; and further characterized by a plant which is vigorous and compact, easy to propagate from cuttings or by budding, with an abundance of disease resistant small glossy foliage and an abundance of flowers borne singly or several to the stem in loose clusters.

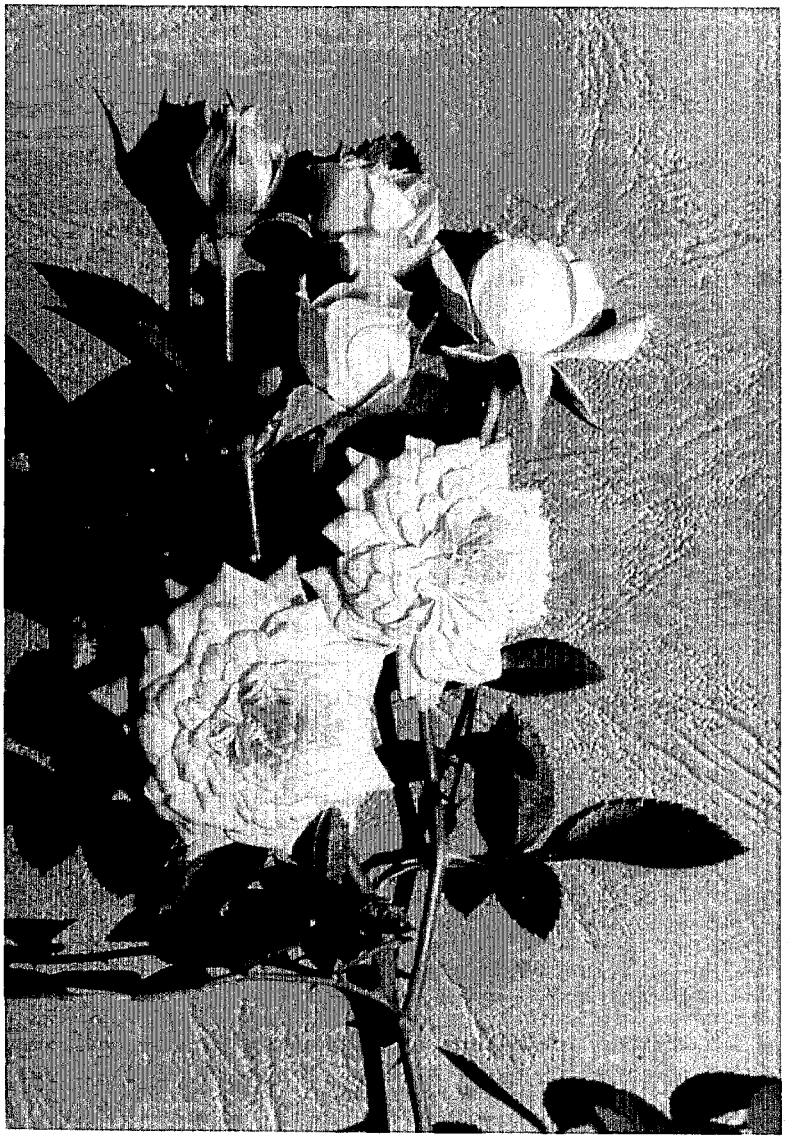

* * * * *